United States Patent [19]

Clark, Jr. et al.

[11] Patent Number: 4,713,479
[45] Date of Patent: * Dec. 15, 1987

[54] SYNTHESIS OF HIGH-PURITY DIALKYL 2-VINYLCYCLOPROPANE-1,1-DICARBOXYLATE

[75] Inventors: Clarence E. Clark, Jr., Cincinnati; Richard G. Fayter, Jr., Fairfield, both of Ohio

[73] Assignee: National Distillers and Chemical Corporation, New York, N.Y.

[*] Notice: The portion of the term of this patent subsequent to Dec. 15, 2004 has been disclaimed.

[21] Appl. No.: 936,004

[22] Filed: Nov. 28, 1986

[51] Int. Cl.$^4$ .................................... C07C 69/743
[52] U.S. Cl. .................................................. 560/124
[58] Field of Search ........................................ 560/124

[56] References Cited

U.S. PATENT DOCUMENTS

| | | | |
|---|---|---|---|
| 4,252,739 | 2/1981 | Fayter | 560/124 |
| 4,321,406 | 3/1982 | Fayter | 560/124 |
| 4,328,168 | 5/1982 | Fayter | 560/124 |

Primary Examiner—Michael L. Shippen
Attorney, Agent, or Firm—Kenneth D. Tremain; Gerald A. Baracka

[57] ABSTRACT

This invention relates to a two-step synthesis of high purity dialkyl 2-vinyl-cyclopropane-1,1-dicarboxylate in which a mixture of trans- and cis-1,4-dihalobutene-2 is first isomerized to essentially trans-1,4-dihalobutene-2 followed immediately by cyclocondensing the resultant trans-1,4-dihalobutene-2 with a malonic ester in the presence of an alcoholic solution of a metallic alkoxide.

8 Claims, No Drawings

SYNTHESIS OF HIGH-PURITY DIALKYL 2-VINYLCYCLOPROPANE-1,1-DICARBOXYLATE

BACKGROUND OF THE INVENTION

G. S. Skinner, et al. first reported the condensation of 1,4-dihalo-2-butene and diethyl malonate in J. Am. Chem. Soc., 72, 1648(1950). The condensation was conducted under anhydrous conditions by reacting the dihalide with the pre-formed disodio anion of the malonic ester in an attempt to synthesize spirocyclopentane-1,5-barbiturates. Kierstead, et al. (J. Chem. Soc., 1952, 3610–21 and J. Chem. Soc., 1953, 1799) reported the preparation of diethyl 2-vinylcyclopropane-1,1-dicarboxylate by the condensation of 1,4-dibromo-2-butene and ethyl sodiomalonate and observed that continual attack by malonate and anion on the 2-vinylcyclopropane derivative produced side products, one of which was 2-vinylbutane-1,1,4,4-tetracarboxylate. Kierstead, et al. also extended the general reaction to ethyl cyanoacetate and ethyl acetoacetate to obtain the corresponding 2-vinylcyclopropane derivatives. In an attempt to develop a new synthetic route for the preparation of the cyclopentane counterparts by deoxyribonucleosides, Murdock, et al. in J. Amer. Chem. Soc., 27, 2395 (1962) reported condensing cis-1,4-dichlorobutene-2 with sodiomalonic ester under anhydrous conditions as the first step in their reaction sequence.

With all of the above reactions, as well as in other reports dealing with the condensation of malonic esters with 1,4-dihalo-2-butenes, e.g. Birch, et al., J. Org. Chem. 23, 1390 (1958); Schmid, et al., J. Org. Chem. 32, 254 (1967); Stewart, et al., J. Org. Chem., 34, 8 (1969), the metal alkoxide and malonic ester were prereacted to first form the corresponding sodiomalonate anion, which was then very slowly added to the dihalobutene. This procedure was considered essential for the successful conduct of the reaction and to optimize the yield of the vinylcyclopropane dicarboxylate. The dihalo compound was not combined directly with the alcoholic caustic to avoid ether by-product formation since this is a well known and widely used procedure (Williamson synthesis) for the preparation of ethers. By adding the malonate anion to the dihalobutene and carefully controlling the rate of this addition, it was believed that linear diaddition products formed by either continued attack on the vinylcyclopropane product by malonate anion or reaction of both the halogens on a single molecule would be minimized. Strictly anhydrous conditions were employed throughout the entire reaction procedure, i.e. during the formation of the anion and the addition of the anion to the dihalobutene, since it is generally accepted that for malonate and acetoacetic ester condensations the presence of water is detrimental (Practical Organic Chemistry, A. I. Vogel, 3rd Ed., Longmans, Green and Co., Ltd., London (1967) pp. 481–486). Even as late as 1970 the classical procedure first developed by Skinner and coworkers was still being used as evidenced by the report of Den Besten, et al. (J. Chem. Eng. Data, 15, 453 (1970)) who prepared diethyl 2-vinylcyclopropane-1,1-dicarboxylate for subsequent thermal decomposition.

In view of the complex state of the reagents, the requirement to operate under strictly anhydrous conditions and the necessity for a sophisticated reaction vessel to carry out the detailed addition, it has heretofore not been practical to prepare vinylcyclopropane derivatives on a commercial scale via such condensation reactions.

U.S. Pat. Nos. 4,328,168 and 4,328,169 inter alia, describe improved processes for the preparation of vinylcyclopropane derivatives. These processes are adaptable to commercial operation and involve reacting, in a fluid state, an alkylating agent, e.g. 1,4-dichlorobutene-2, and an activated methylene compound, e.g. dimethyl malonate, in the presence, respectively, of a cyclic polyether compound or an alkylene oxide derivative and an alkali metal compound. A wide variety of cyclopropane derivatives are readily obtained by these processes.

Another process which has met with favor in overcoming the disadvantages of the earlier literature processes is the phase-transfer-catalyzed synthesis of vinylcyclopropane derivatives described in U.S. Pat. No. 4,252,739, among others, and which involves reacting an alkylating agent, e.g. 1-4-dichlorobutene-2, and an activated methylene compound, e.g. a lower alkyl malonate in the presence of an onium compound, an alkali metal compound and water. While this process works well with certain lower alkyl esters of 2-vinylcyclopropane-1,1-dicarboxylate, for example the ethyl and higher esters, it produces lower yields of the order of <10% when dimethyl 2-vinylcyclopropane-1,1-dicarboxylate is sought to be obtained. It appears that the phase-transfer process when directed to the synthesis of the dimethyl ester produces low yields due to ester saponification which is apparently competitive with the condensation reaction in the presence of methyl esters but which saponification is insignificant with the ethyl and higher esters.

It would be highly desirable, therefore, if an improved process for the preparation of di lower alkyl 2-vinylcyclopropane-1,1-dicarboxylates by the reaction of 1,4-dihalobutenes and malonic esters were available which did not possess the drawbacks of the prior art processes. It would also be desirable if it were possible to eliminate the need for conducting the process in a stepwise manner, i.e., preforming the anion, and if the need for maintaining strictly anhydrous conditions could be eliminated and if the yield of the desired product could be increased, the process would have even greater utility. These and other advantages are realized by the improved process of this invention.

The starting material for the condensation of 1,4-dihalobutene-2 is preferably 1,4-dichlorobutene-2 and as a commercial product this is usually composed of three isomeric dichlorobutenes, trans-1,4-dichlorobutene-2, cis-1,4- dichlorobutene-2 and 3,4-dichlorobutene-1. Trans-1,4- dichlorobutene-2 is the preferred starting material as the stereochemistry of the intermediate (I) is such that the desired dimethyl 2-vinyl-cyclopropane-1,1-dicarboxylate is the exclusive product. This is illustrated in Mechanism I below:

MECHANISM I

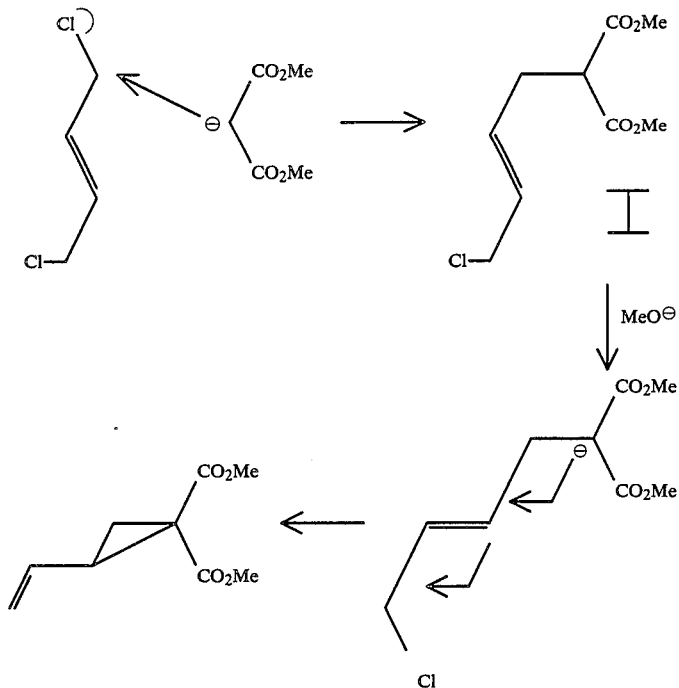

Cis-1,4-dichlorobutene-2 gives two products, dimethyl 2-vinylcyclopropane-1,1-dicarboxylate and dimethyl cyclopent-3-ene-1,1-dicarboxylate in nearly equal amounts as shown in Mechanism II below.

MECHANISM II

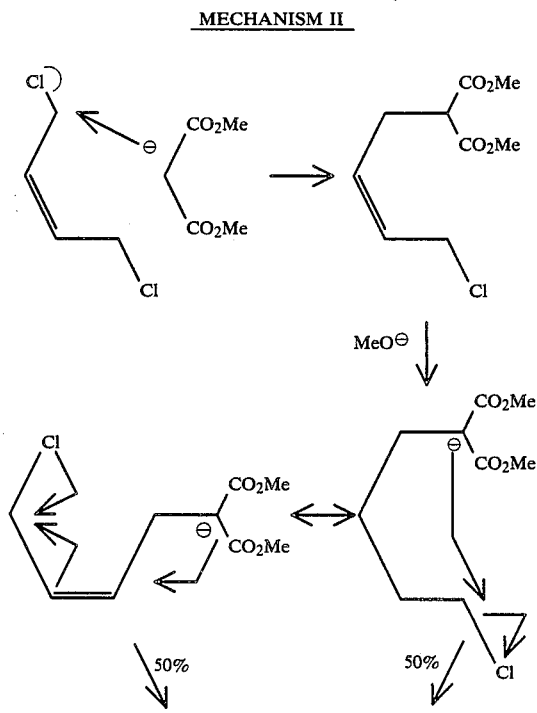

-continued
MECHANISM II

It is nearly impossible to separate dimethyl cyclopent-3-ene-1,1-dicarboxylate from the desired dimethyl 2-vinylcyclopropane-1,1-dicarboxylate by any reasonable means. In the described condensation reaction the third isomer, 3,4-dichlorobutene-1 gives only useless elimination products.

Fractional distillation of the three dichlorobutene isomers can readily be accomplished, but this is an expensive process and leads to the additional difficulty and cost of disposing of 3,4-dichlorobutene-1 and cis-1,4-dichlorobutene-2.

Efforts have been made in terms of isomerizing cis-1,4-dichlorobutene-2 to trans-1,4-dichlorobutene-2, but these methods have met with only moderate success.

Heterogeneous iron, tin and copper compounds as well as onium salts have been reported in the literature as dichlorobutene isomerization catalysts. A typical process employing a copper catalyst is disclosed in U.S. Pat. No. 2,911,450. However, such processes are not completely satisfactory as they either have proven to be ineffective in some instances or have given equilibrium mixtures of all three dichlorobutenes.

The use of thiols as cis-to-trans-olefin isomerization catalysts has also been reported in the literature. See, W. G. Niehaus, Jr., *Bioorg. Chem.*, 3(3), 302–10 (1974) and C. Walling, et al., *J. Amer. Chem. Soc.*, 81, 1144–8 (1959) as has hydrogen bromide-catalyzed isomerization. See N. P. Neureiter, et al., *J. Amer. Chem. Soc.*, 82, 5345–8 (1960). However, the thiol-catalyzed and hydrogen bromide-catalyzed isomerization of olefins typically leads to an equilibrium mixture of approximately 80% trans- and 20% cis-olefin. This appears to be true regardless of whether the starting olefin is cis or trans. See C. Walling, et al. Ibid.

It would be highly desirable, therefore, if an improved process could be developed which would permit an efficient cis-to-trans isomerization of 1,4-dichlorobutene-2 so that a high trans (>90%) mixture could be obtained from the usual commercial mixture of 1,4-dichlorobutene-2, which normally has a trans/cis ratio of 77/23, or from other mixtures having even lower trans content without any of the attendant disadvantages of the prior art.

It would also be highly desirable to provide a product with a high content of trans-1,4-dichlorobutene-2 and being substantially free from the other two isomers cis-1,4-dichlorobutene-2 and 3,4-dichlorobutene-1, which in the described condensation reaction with malonic esters either give approximately equal amounts of the desired dimethyl 2-vinylcyclopropane-1,1-dicarboxylate and the unwanted dimethyl cyclopent-3-ene-1,1-dicarboxylate or in the case of the isomeric 3,4-dichlorobutene-1 only useless elimination products.

It is, therefore, an object of the present invention to provide an improved process for the production of di lower alkyl 2-vinylcyclopropane-1,1-dicarboxylates by the reaction of 1,4-dihalobutenes and malonic esters which does not have the drawbacks associated with the prior art processes.

It is a further object of the present invention to provide a process of preparing high yields of dimethyl 2-vinylcyclopropane-1,1-dicarboxylate without the attendant saponification of the ester with resulting low yields of the desired product as has been observed in the prior art processes.

It is still a further object of the invention to provide a process which also readily produces an efficient cis-to-trans isomerization of 1,4-dichlorobutene-2 so as to provide a high trans content greater than 90% which may be readily condensed with malonic esters to provide excellent yields of dimethyl 2-vinylcyclopropane-1,1-dicarboxylate with greater than 95% purity.

These and other objects of the present invention are readily achieved by the novel process hereinafter described.

BRIEF SUMMARY OF THE INVENTION

The objects of the present invention are readily achieved and high-purity dialkyl 2-vinyl-cyclopropane-1,1-dicarboxylate is readily obtained by a two-step "one-pot" synthesis with minimum contamination by dialkyl cyclopent-3-ene-1,1-dicarboxylate using inexpensive, readily available starting materials.

As stated earlier, pure dialkyl 2-vinylcyclopropane-1,1-dicarboxylate requires pure trans 1,4-dichlorobutene-2 as the starting material and this is efficiently accomplished by the present process in which a commercially available 80/20 trans/cis-1,4-dichlorobutene-2 mixture is isomerized in the first step of the reaction to a 95/5 trans/cis mixture in a relatively few minutes. The isomerization is followed immediately in the same reaction vessel by cyclocondensation with dialkyl malonate in the presence of an alcoholic solution of a metallic alkoxide. The desired product, dialkyl 2-vinylcyclopropane-1,1-dicarboxylate is obtained in high yield (75–80% distilled) with only 2–3% contamination by dialkyl cyclopent-3-ene-1,1-dicarboxylate.

DETAILED DESCRIPTION OF THE INVENTION

The present invention comprises first isomerizing mixtures of cis-and-trans-1,4-dichlorobutene-2 to a high level of trans-1,4-dichlorobutene-2 by the catalytic influence of thiols or anhydrous hydrogen bromide or hydrogen chloride with ultraviolet light and/or chemical initiators so that an 80/20 trans/cis mixture is isomerized to a 95/5 trans/cis mixture in as little as ten minutes followed immediately by the cyclocondensation with dialkyl malonate and metallic alkoxide.

The temperature of the isomerization reaction is not critical and may conveniently be from room temperature up to 80° C. or higher depending upon the catalyst employed for the isomerization.

Likewise, the amount of catalyst is not critical and may conveniently be from 0.5 mole % based on the weight of the dichlorobutene to about 20 mole % and preferably from 5 mole % to 10 mole %.

The time of the reaction is likewise not critical and depends to some extent upon the catalyst employed for the isomerization. Thus with the thiol catalyzed isomerization the time may range from 30 minutes to an hour or more at reaction temperatures of from 70° C. to 90° C. whereas with the anhydrous hydrogen bromide or chloride catalyzed isomerization the time is frequently from twenty to thirty minutes or so at temperatures preferably at about room temperature.

With both the thiol catalyzed and hydrogen bromide and chloride catalyzed isomerizations, ratios better than 93/7 trans/cis- dichlorobutene-2 have consistently been obtained with 95–97% recovery of the dichlorobutene-2.

The cyclocondensation of the isomerized 1,4-dichlorobutene-2 with the malonic esters is preferably carried out in the presence of an inert organic solvent, e.g. a lower alcohol, at reflux temperatures. Preferably the procedure involves the rapid addition of 25% methanolic sodium methoxide to a solution of 1,4-dichlorobutene-2 and dimethyl malonate in minimum amount of methanol. The reaction temperature is maintained at 65°–70° C. by methanol reflux and maintenance of a low temperature by the slow addition of methoxide is not needed. After the reaction is complete, the mixture is vacuum filtered, neutralized preferably with concentrated hydrochloric acid and filtered a second time to complete the removal of all salts. The solvent is then removed under vacuum to produce a yield of crude product of 80–85%. Final vacuum distillation produces a product of 75–80% yield.

Suitable organic solvents for the reaction include the lower alcohols, for example, methanol, ethanol, propanol, and the like, methanol being preferred for ease of handling.

Suitable metallic alkoxides include, for example, sodium or potassium methoxide, ethoxide, propoxide, butoxide, and the like. Again, a methanolic sodium methoxide solution is preferred.

The reaction may be neutralized with any strong mineral acid, e.g. sulfuric acid, hydrochloric acid, etc.

Typical thiols useful in the described isomerization reaction are 2-mecaptoethanol, thiophenol, thiolacetic acid, methanethiol, thioglycolic acid, mercaptosuccinic acid, etc.

In the thiol catalyzed isomerization of the dihalobutenes as well as in the anhydrous hydrogen bromide or chloride isomerization reaction it is necessary to employ an initiator for the reaction. Typical chemical initiators may be, for example, 2,2'-azobisisobutyronitrile (AIBN), benzoyl peroxide, t-butyl peroxide, etc.

The amount of chemical initiator employed in the reaction is not critical but must be present in sufficient amount to initiate the reaction. Typically from about 0.1 mole % to about 5 mole % based on the weight of the dichlorobutene has been found to be effective.

As indicated above, 2-mercaptoethanol as the catalyst and 2,2'-azobisisobutyronitrile (AIBN) as the initiator are preferred and have been found to be highly useful in the isomerization of dichlorobutene as they consistently provide ratios greater than 93/7 trans/cis-dichlorobutene with 95-97% recovery of the dichlorobutenes.

Hydrogen bromide with either AIBN or ultraviolet light has also been found to be effective in producing remarkably high trans/cis (95/5) ratios of dichlorobutene at room temperature.

Hydrogen bromide is the preferred catalyst in the described reaction and has been found to be equally effective with either AIBN or ultraviolet light initiation. However, 2-mercaptoethanol with ultraviolet light and hydrogen chloride with ultraviolet light showed marginal activity and hydrogen iodide and $I_2$ showed no catalytic activity with either AIBN or ultraviolet light.

Suitable halogenated olefins for use in the present invention include:

1,4-dichlorobutene-2; 1,4-dibromobutene-2; 1-bromo-4-chlorobutene-2; 1,4-dichloro-2-methylbutene-2; 1,4-dibromo-2-methylbutene-2; 1,4-dichloro-2,3-dimethylbutene-2; 1,4-dibromo-2,3-dimethylbutene-2; 1,4-dichloropentene-2; 1,4-dibromopentene-2; 1,4-dichloro-4-methylpentene-2; and 1,4-dibromo-4-methylpentene-2;

1,4-Dichloro- and 1,4-dibromobutene-2 are particularly useful for the present process in view of their commercial availability, reactivity and ability to yield highly useful vinylcyclopropane derivatives with minimal undesirable by-product formation.

Suitable malonic esters for use in the present process are the lower alkyl malonates, such as dimethyl malonate, diethyl malonate, dibutylmalonate, disopropyl malonate, ethyl(N,N-dimethyl-2-aminoethyl)malonate, and di(N,N-dimethyl-2-aminoethyl)malonate and the like, dimethyl malonate being preferred because of its ready availability.

The invention will be described in greater detail in conjunction with the following specific examples in which the parts are by weight unless otherwise specified.

EXAMPLE 1

Dimethyl 2-Vinylcyclopropane-1,1-dicarboxylate (Comparative example—not part of the present invention)

Sodium methoxide (108.02 g, 2.0 moles) 25% in MeOH was added slowly (~2.25 hrs.) to dimethyl malonate (132.12 g, 1.0 mole) in a heated and stirred flask having a bottom opening; 200 mL additional MeOH was required to maintain fluidity of the slurry. The sodiomalonate was then added (~30 min.) through the bottom opening to 1,4-dichlorobutene-2 (125 g, 1.0 mole) in a second heated and stirred flask. The mixture was heated at reflux ~4.5 hours, cooled, and vacuum filtered. The clear filtrate was then concentrated under vacuum at which point additional salts precipitated. An attempted second filtration was unsuccessful due to the slimy cake, and the salts were finally removed by centrifuging to give 146 g of crude product. Vacuum distillation (60°/0.4 mm–90°/0.55 mm) gave a small forecut, 87.6 g of product (47.6% yield), and 44.5 g of residue.

EXAMPLE 2

Combined HBr-catalyzed Isomerization and Cyclocondensation

~80% Trans-1,4-dichlorobutene-2 (150 g, 1.2 moles) and 2,2'-azobisisobutyronitrile (AIBN) (3.94 g, 0.024 mole) were heated with stirring to 60° C. at which point HBr gas addition was started. After 10 minutes, heating and gas flow were terminated (~94/6 trans/cis by GC) and the reaction allowed to cool with $N_2$ purge to remove HBr. Dimethylmalonate (132.12 g, 1.0 mole) in 50 mL of MeOH was then added to the flask. NaOMe (108.02 g, 2.0 moles) 25% in MeOH was added in 17 minutes and the reaction allowed to cool (80.5% dimethyl 2-vinylcyclopropane-1,1-dicarboxylate and 3.3% dimethyl cyclopent-3-ene-1,1-dicarboxylate by GC). After workup and distillation as above, 139.2 g (75.6% yield) of product consisting of 95.5% dimethyl 2-vinylcyclopropane-1,1-dicarboxylate and 4.5% dimethyl cyclopent-3-ene-1,1-dicarboxylate was obtained.

EXAMPLE 3

Combined Thiol-catalyzed Isomerization and Cyclocondensation

To ~80% trans-, 20% cis-1,4-dichlorobutene-2 (150 g, 1.2 moles) was added 2-mercaptoethanol (7.03 g, 0.09 moles) and AIBN (1.9 g, 0.0116 moles). The mixture was then heated at 80° C. with stirring for 30 minutes at which point the trans/cis ratio was ~92/8. After cooling to 23° C., and without further treatment, the cyclocondensation, workup, and distillation were conducted as in Example 2. Distillation afforded 114 g of product containing 95.5% dimethyl 2-vinylcyclopropane-1,1-dicarboxylate and 4.5% dimethyl cyclopent-3-ene-1,1-dicarboxylate.

What is claimed is:

1. A process of preparing dialkyl 2-vinyl-cyclo-propane-1,1-dicarboxylates which comprises the two-step reaction sequence of:
   (a) contacting a mixture of trans-1,4-dihalobutene-2 and cis-1,4-dihalobutene-2 with a thiol catalyst or a hydrogen bromide or hydrogen chloride catalyst and an initiator for the reaction at a temperature from about 25° C. to about 80° C. and for a time sufficient to permit the conversion of substantially all of the cis-1,4-dihalobutene-2 to trans-1,4-dihalobutene-2, thereafter;
   (b) cyclocondensing a di lower alkyl malonic ester with said trans-1,4-dihalobutene-2 in the presence of an alcoholic solution of a metallic alkoxide and recovering the high purity dialkyl 2-vinylcyclopropane-1,1-dicarboxylate so produced.

2. The process according to claim 1 in which the dihalobutene is 1,4-dichlorobutene-2.

3. The process according to claim 1 in which the dihalobutene is 1,4-dibromobutene-2.

4. The process according to claim 1 in which the catalyst is 2-mercaptoethanol.

5. The process according to claim 1 in which the intiator is 2,2'-azobisisobutyronitrile.

6. The process according to claim 1 in which the intiator is ultraviolet light.

7. The process according to claim 1 in which the catalyst is anhydrous hydrogen bromide.

8. The process according to claim 1 in which the malonic ester is dimethyl malonate.

* * * * *

UNITED STATES PATENT AND TRADEMARK OFFICE
CERTIFICATE OF CORRECTION

PATENT NO. : 4,713,479
DATED : December 15, 1987
INVENTOR(S) : Clarence E. Clark, Jr. and Richard G. Fayter, Jr.

It is certified that error appears in the above-identified patent and that said Letters Patent are hereby corrected as shown below:

Column 3, the formula under MECHANISM I should read:

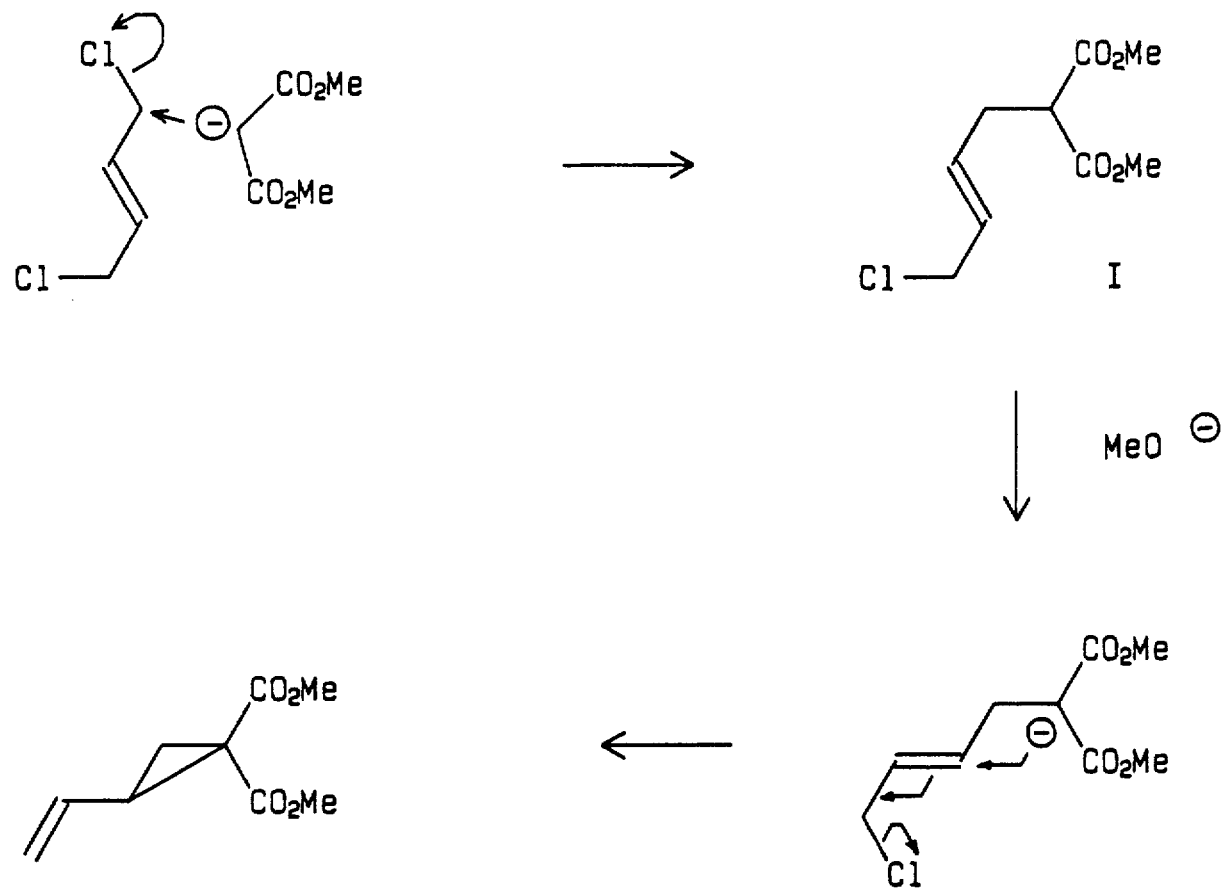

UNITED STATES PATENT AND TRADEMARK OFFICE
CERTIFICATE OF CORRECTION

PATENT NO. : 4,713,479
DATED : December 15, 1987
INVENTOR(S) : Clarence E. Clark, Jr. and Richard G. Fayter, Jr.

It is certified that error appears in the above-identified patent and that said Letters Patent are hereby corrected as shown below:

Columns 3 and 4, the formula under <u>MECHANISM II</u> should read:

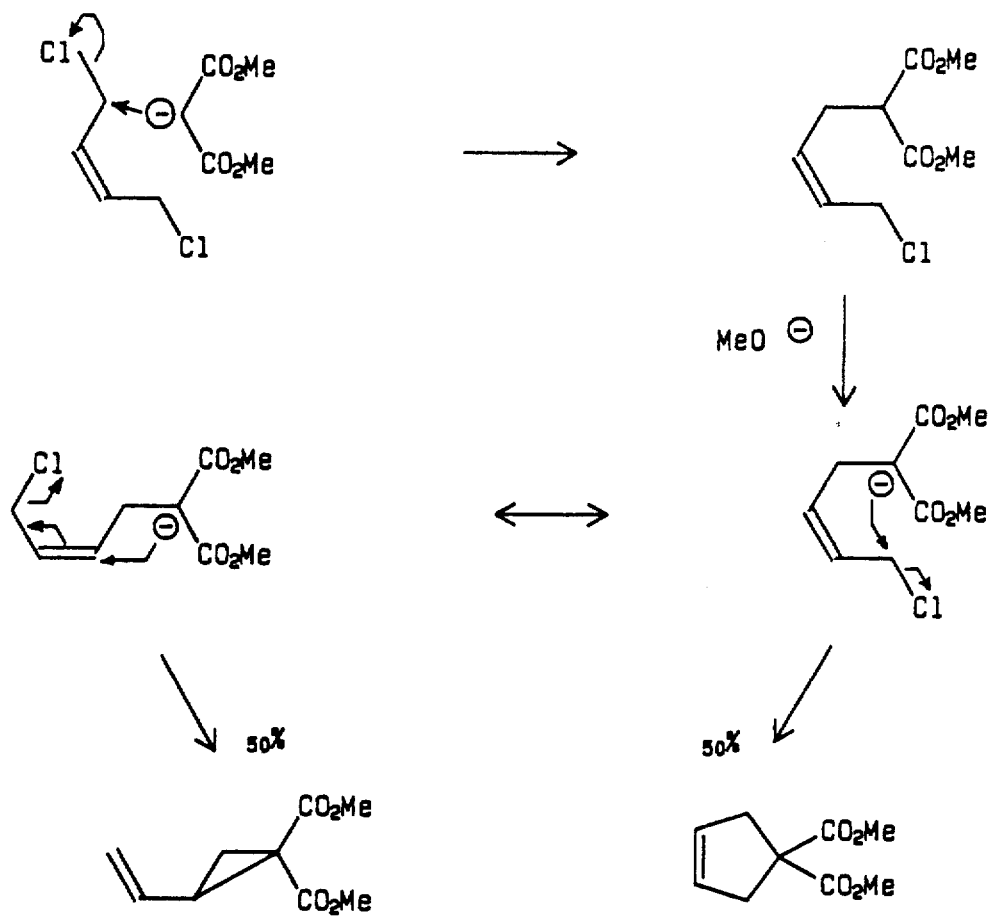

UNITED STATES PATENT AND TRADEMARK OFFICE
CERTIFICATE OF CORRECTION

PATENT NO. : 4,713,479
DATED : December 15, 1987
INVENTOR(S) : Clarence E. Clark, Jr. and Richard G. Fayter, Jr.

It is certified that error appears in the above—identified patent and that said Letters Patent are hereby corrected as shown below:

Claim 1, line 1, "2-vinyl-cyclo-pro-" should read --- 2-vinylcyclopro- ---.

Claim 5, line 2, "intiator" should read --- initiator ---.

Claim 6, line 2, "intiator" should read --- initiator ---.

Signed and Sealed this

Twelfth Day of July, 1988

Attest:

DONALD J. QUIGG

Attesting Officer

Commissioner of Patents and Trademarks